United States Patent [19]

Aoki

[11] Patent Number: 4,542,167

[45] Date of Patent: Sep. 17, 1985

[54] DENTAL CEMENT COMPOSITION COMPRISING HYDROXYAPATITE AND ACRYLIC ACID/ITACONIC ACID COPOLYMER HARDENER

[76] Inventor: Hideki Aoki, 34-1, Morinosato, Kukisaki-cho, Inashiki-gun, Ibaraki-ken, Japan

[21] Appl. No.: 606,125

[22] Filed: May 1, 1984

[51] Int. Cl.$^4$ .............................................. C08L 33/02
[52] U.S. Cl. .................................. 523/109; 106/35; 523/116
[58] Field of Search .................. 523/109, 116; 106/35

[56] References Cited

U.S. PATENT DOCUMENTS

| | | | |
|---|---|---|---|
| 4,097,935 | 7/1978 | Jarcho | 106/35 |
| 4,149,893 | 4/1979 | Aoki et al. | 106/35 |
| 4,433,958 | 2/1984 | Fellman et al. | 106/35 |
| 4,451,235 | 5/1984 | Okuda et al. | 106/35 |

Primary Examiner—Harold D. Anderson
Attorney, Agent, or Firm—Paul & Paul

[57] ABSTRACT

A water-hardenable dental cement composition comprising hydroxyapatite [$Ca_{10}(PO_4)_6(OH)_2$] as the main component and an inorganic powder and a hardening agent.

3 Claims, 3 Drawing Figures

DENTAL CEMENT COMPOSITION COMPRISING HYDROXYAPATITE AND ACRYLIC ACID/ITACONIC ACID COPOLYMER HARDENER

BACKGROUND OF THE INVENTION

1. Field of the Invention

The present invention relates to a water-hardenable dental cement composition.

A water-hardenable dental cement composition provided according to the present invention comprises hydroxyapatite as the main component and a specific inorganic powder and an unsaturated carboxylic acid or a copolymer of an unsaturated carboxylic acid with other organic compound. This dental cement composition is a new type of a dental cement. The dental composition of the present invention has a reduced irritation to the dental pulp cells and has an excellent reactivity with saliva.

2. Description of the Prior Art

Zinc phosphate cement and carboxylate cement have heretofore been used as the dental cement. These known cements, however, are defective and improvements have been desired. For example, zinc phosphate cement has a high compression strength but it is irritative to the dental pulp. Carboxylate cement is low in the compression strength and when it is formed into a cement liquid, the viscosity is too high and kneading is difficult.

Water-hardenable carboxylate cement has recently been developed, and this water-hardenable cement is improved over the known carboxylate cement in the operation adaptability and it shows an increased compression strength. However, this water-hardenable carboxylate cement is still insufficient in the reactivity with saliva.

Dental cement should satisfy the requirement that it should be kept in the form of a hardened body in the oral cavity without disintegration. All of the above-mentioned known cements are disintegrated in a short time if they fall in contact with saliva in the oral cavity, resulting in falling of repaired portions, and they are insufficient as permanent filling materials.

Under this background, development of dental cement having a high compression strength and an excellent operation adaptability and being capable of providing a hardened body which can be permanently maintained in good conditions without disintegration due to the action of saliva has been desired in the field of dental surgery, but this desire has not been satisfied.

SUMMARY OF THE INVENTION

We made research with a view to developing dental cement meeting these requirements, and we established the technique of providing dental cement desired in the art, that is, water-hardenable dental cement having the above-mentioned properties and we have now completed the present invention.

The present invention thus provides a water-hardenable dental cement composition comprising hydroxyapatite [$Ca_{10}(PO_4)_6(OH)_2$] as the main component and an inorganic powder and a hardening agent.

The water-hardenable dental cement of the present invention comprises hydroxyapatite as the main component, and in this point, the dental cement of the present invention can be clearly distinguished from the known dental cements. In short, a new type of dental cement is provided according to the present invention.

DESCRIPTION OF THE PREFERRED EMBODIMENTS

Figure 1:
FIG. 1 is a microscope photograph showing the result of the test of reaction of a hardened body of the hydroxyapatite-containing cement of the present invention with the total saliva in the oral cavity.

The compression strength of the dental cement of the present invention is sufficiently high and is excellent in the operation adaptability. Furthermore, the dental cement of the present invention has reduced irritation to tissue cells in the oral cavity and dental pulp cells and it has a surprisingly high resistance to saliva. Namely, it must be noted that when a hardened body of the dental cement composition falls in contact with saliva in the oral cavity, the surface of the hardened nody is converted to an enameled surface, and disintegration of the hardened body by the action of saliva is hardly caused and the hardened body can be permanently maintained in good conditions.

In view of the above-mentioned properties and from the results of repeated experiments, it is expected that the dental cement of the present invention will be effectively used as a permanent filling material, though this use cannot be expected at all for the conventional dental cements.

Hydroxyapatite used as the main component in the dental cement of the present invention is represented by the formula $Ca_{10}(PO_4)_6(OH)_2$, and hydroxyapatite is prepared, for example, according to a process proposed by me in the specification of Japanese Unexamined Patent Publication (Kokai) No. 53-81499.

This hydroxyapatite is ordinarily available in the form of a lowly crystalline powder. However, when hydroxyapatite is incorporated in the cement composition of the present invention, it may preferably be sintered at a temperature higher than 1000° C. to effect growth of crystals, and hydroxyapatite is used in the form of a highly crystalline powder having a particle size smaller than 200 mesh.

The inorganic powder may be at least one member selected from powders (having a size of 200 to 400 mesh) of calcium tertiary phosphate, calcium oxide, zinc oxide, silicon oxide, aluminum oxide, magnesium oxide and calcium fluoride. If the inorganic powder is a mixture of two or more of the foregoing powders, the mixing ratio may be selected, for example, from those shown in the table in Example 2 given hereinafter.

Calcium tertiary phosphate is effective for increasing the strength of cement. Zinc oxide and calcium oxide have an effect of shortening the hardening time of cement and they react with acrylic acid to exert an effect of reducing the disintegrating property of cement. Other inorganic substances, that is, silicon oxide, aluminum oxide, magnesium oxide and calcium fluoride, are effective for increasing the compression strength.

As the unsaturated carboxylic acid, there can be mentioned, for example, acrylic acid, methacrylic acid, ethacrylic acid, itaconic acid and fumaric acid. As the other organic compound copolymerized with the unsaturated carboxylic acid, there can be mentioned, for example, methyl methacrylate, methyl acrylate, ethyl acrylate, vinyl acetate, methylvinyl ether, ethylvinyl ether and vinylpyrrolidone. Each of these unsaturated carboxylic acids and copolymers of unsaturated carboxylic acids with other organic compounds has a water-hardening property.

In the dental cement composition of the present invention, it is required that the unsaturated carboxylic acid or its copolymer with other organic compound should be incorporated in the form of a solid powder. The particle size of this powder may be in the range of from 200 to 400 mesh and the powder may be incorporated in an amount of 10 to 50% by weight based on the total composition.

In the dental cement composition of the present invention, the above-mentioned inorganic powder is incorporated for increasing the strength and controlling the hardening time, and the unsaturated carboxylic acid or its copolymer is incoporated as the hardening agent.

The dental cement composition of the present invention is obtained by adding a predetermined amount (20 to 80% by weight) of the inorganic powder to a predetemined amount (80 to 20% by weight) of the powdery hydroxy apatite, pulverizing and uniformly blending the mixture by optional means, sintering the mixture at a temperature of 1000° to 1400° C. under atmospheric pressure for 1 to 5 hours, cooling the sintered mixture to normal temperature, and homogeneously incorporating a predetermined amount (10 to 50% by weight based on the total composition) of the powder of the hardening agent.

The present invention will now be described in detail with reference to the following examples.

EXAMPLE 1

A hydroxyapatite powder sintered at 1250° C. for 1 hour was mixed with a ZnO powder sintered at 1200° C. for 1 hour at a weight ratio of 1:1, 1:2, 1:3 or 1:4. Then, the mixture was mixed with polyacrylic acid at a weight ratio of 75:25, and the resulting mixture was pulverized and blended and particles having a size smaller than 200 mesh were recovered by classification.

Each of the so-obtained four dental cement compositions was kneaded at a water-mixing ratio (water/dental cement powder32 W/P) of 0.5/1.5 in the same manner as conventionally adopted for carboxylate cement.

When the hardening time was measured by using a Vickers needle according to the JIS Standards, it was found that in each case, the hardening time was about 10 minutes, which hardening time is in agreement with the hardening time of ordinary dental cement.

When the compression strength was measured, it was found that the above samples had compression strengths of 900, 700, 500 and 300 Kg/cm$^2$, respectively. Thus, it was confirmed that the strength is increased in proportion to the amount of hydroxyapatite. The hardened body having a highest strength and a hardened body of carboxylate cement free of hydroxyapatite were thrown into the human oral cavity and reacted with the total saliva for 20 hours.

Figure 2:
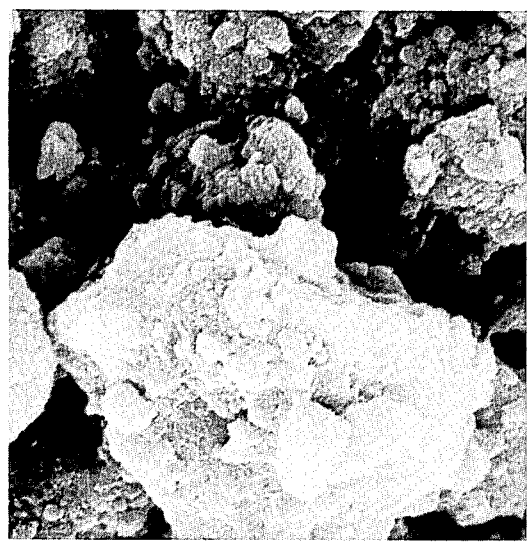
FIG. 2 is a micrograph showing the result of the test of reaction of a hardened body of the hydroxy-apatite-free cement with the total saliva in the oral cavity; and, FIG. 3 is a graph showing cell propagation curves of various cements.

When the surfaces of the hardened bodies were examined by a scanning type electron microscope, photos shown in FIG. 1 and 2 were obtained.

The photo shown in FIG. 1 shows the surface of the hydroxyapatite-containing cement.

The photo shown in FIG. 2 shows the surface of the hydroxyapatite-free cement.

As is seen from these photos, the surface of the hydroxyapatite-containing cement has none of convexities and concavities and resembles an enamel surface.

It was also confirmed that the disintegrating property of the hydroxyapatite-containing cement is much lower than that of the hydroxyapatite-free cement.

EXAMPLE 2

Cement compositions were prepared from hydroxyapatite as the main component, 15 to 45% by weight of acrylic acid and inorganic powders in amounts shown in Table 1. The compositions were kneaded at a water-mixing ratio of from 1.0 to 4.0. The hardening time was in the range of from about 5 to about 15 minutes. When the compression strengths of hardened bodies were measured, it was found that the maximum compression strength was 1100 Kg/cm$^2$, which is comparable to that of zinc phosphate cement known to have a highest strength among dental cements.

TABLE 1

| Run No. | Acrylic Acid | Hydroxy-apatite | $Ca_3(PO_4)_2$ | CaO | ZnO | $Al_2O_3$ | $SiO_2$ | MgO | $CaF_2$ | Compression Strength (kg/cm$^2$) |
|---|---|---|---|---|---|---|---|---|---|---|
| 1 | 15 | 60 | | | 25 | | | | | 500 |
| 2 | 15 | 40 | 5 | | 30 | | 10 | | | 1000 |
| 3 | 15 | 30 | 10 | 5 | 30 | 5 | 5 | | | 900 |
| 4 | 15 | 30 | | | 30 | 5 | 10 | 5 | 5 | 1100 |
| 5 | 15 | 30 | | 20 | 15 | | 20 | | | 700 |
| 6 | 25 | 40 | | 5 | 25 | | 5 | | | 800 |
| 7 | 25 | 30 | 5 | 10 | 10 | | 10 | 10 | | 700 |
| 8 | 25 | 30 | | 5 | 30 | 5 | 5 | | | 1000 |
| 9 | 40 | 30 | | | 30 | | | | | 500 |
| 10 | 40 | 30 | | 5 | 20 | | 5 | | | 500 |

Note
The numerical values indicate amonts (% by weight).

EXAMPLE 3

Copolymers of acrylic acid, other unsaturated carboxylic acid and methyl acrylate selected as the other organic compound were prepared. By using these copolymers as the hardening agent, dental cement compositions shown in Table 2 were prepared, and the compression strength was determined.

TABLE 2

| 4/1 Weight Ratio Acrylic Acid/Itaconic Acid Copolymer | 4/1 Weight Ratio Acrylic Acid/Maleic Acid Copolymer | 7/2/1 Weight Ratio Acrylic Acid/Itaconic Acid/Fumaric Acid Copolymer | 4/1 Weight Ratio Acrylic Acid/Methyl Acrylate Copolymer | Hydroxyapatite | ZnO | $Al_2O_3$ | $SiO_2$ | Compression Strength (kg/cm$^2$) |
|---|---|---|---|---|---|---|---|---|
| 20 | | | | 40 | 40 | | | 950 |
| 20 | | | | 40 | 20 | 5 | 15 | 1100 |
| 20 | | | | 50 | | 5 | 25 | 600 |
| | 20 | | | 40 | 40 | | | 700 |
| | 20 | | | 30 | 20 | 10 | 20 | 950 |
| | 20 | | | 20 | | 10 | 50 | 500 |
| | | 20 | | 40 | 40 | | | 800 |
| | | 20 | | 60 | | 20 | | 500 |
| | | 20 | | 60 | 10 | | 10 | 500 |
| | | | 20 | 40 | 40 | | | 700 |
| | | | 20 | 50 | | 5 | 25 | 400 |
| | | | 20 | 30 | | 20 | 30 | 500 |

Note
The numerical values indicate amonts (% by weight).

EXAMPLE 4

The toxicity to cells was tested according to the tissue culture method. L cells were used as the cells and they were cultured in an MEM culture medium to which 10% of calf serum was added. Cement sealed in a glass tube having an inner diameter of 0.3 mm and a length of 5 mm was used as the sample.

2 ml of a cell suspension (MEM+10% calf cerum) containing $1 \times 10^5$ of cells was poured into short test tubes, and the test tubes were placed on an inclined stand having an inclination angle of 10° and culturing was conducted in a thermostat device maintained at 37° C. After 1 day's culturing, the sample sterilized for 2 hours under an ultraviolet ray lamp was placed in the bottom of the test tube. The empty test tube in which the sample was not placed was used as the control.

When 1 day or 2 days had passed form the start of culturing, the number of cells contained in three test tubes of each group was measured. The cells were dyed with 0.1% Crystal Violet, and the nucleus number was counted by a hemocyte counting plate and the cell number was expressed by this nucleus number.

Figure 3:
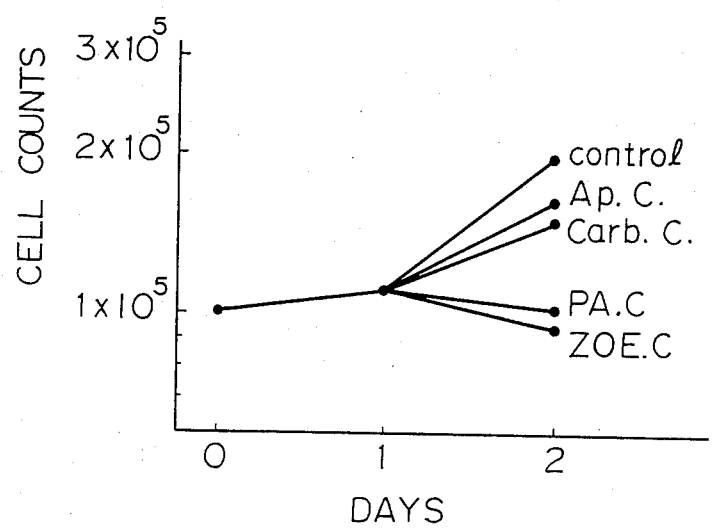

FIG. 3 shows propagation curves obtained in the sample groups and control group. In each case, three test tubes were used and the mean value of the count numbers in these three test tubes was calculated and shown. The standard deviation was about 10%.

In FIG. 3, Control indicates the curve of the control group, and Ap. C. indicates the curve of the hardened body of the dental cement of the present invention comprising 37.5% by weight of hydroxyapatite, 37.5% by weight of zinc oxide and 25% by weight of acrylic acid. Carb. C. indicates the curve of the hardened body of conventional carboxylate cement, PA. C. indicates the curve of the hardened body of cement comprising 25% by weight of polyacrylic acid and 75% by weight of zinc oxide, and ZOE. C. indicates the curve of the hardened body of commercially available zinc oxide eugenol cement. The relative propagations in the samples Ap. C., Carb. C., PA. C. and ZOE. C. based on the control sample after 2 days' culturing were 67%, 55%, 0% and −8%, respectively.

From these data, it is seen that Ap. C. is closest to the control and the toxicity of Ap. C. to the cells was much lower than those of other samples. It is also seen that PA. C. is close to ZOE. C. having a highest toxicity and the toxicity to cells is drastically reduced by addition of hydroxyapatite.

EXAMPLE 5

The false molar on the lower jaw of an adult mongrel dog (middle dog having a body weight of 15 Kg) was bored from the crown portion by a dental turbine to expose the dental pulp, and the hole was filled with cement comprising 20% by weight of acrylic acid, 40% by weight of hydroxyapatite and 40% by weight of zinc oxide or with commercially available carboxylate cement. After 1 week, the false molar was cut out from the root portion under the anesthesia and immediately fixed with formalin.

After the fixation, examination was carried out according to the ordinary phthological histological test method. It was found that as in case of the toxicity test using cultured cells, the dental pulp-irritating property of the hydroxyapatite-containing cement is lower than that of carboxylate cement which is said to be lowest in the dental pulp-irritating property among known dental cements.

I claim:

1. A water-hardenable dental cement composition comprising hydroxyapatite ($Ca_{10}(PO_4)_6(OH)_2$) as the main component and an inorganic powder and a hardening agent consisting of a copolymer of acrylic acid with itaconic acid.

2. A water-hardenable dental cement composition as set forth in claim 1, wherein the inorganic powder is at least one member selected from calcium tertiary phosphate, calcium oxide, zinc oxide, silicon oxide, aluminum oxide, magnesium oxide, or calcium fluoride.

3. A water-hardenable dental cement composition as set forth in claim 1, wherein the inorganic powder is added to hydroxy apatite at a weight ratio of 4:1 to 1:4 and the hardening agent is added to the mixture at a weight ratio of 1:9 to 5:5.

* * * * *